United States Patent [19]

Leiboff

[11] Patent Number: 4,625,727
[45] Date of Patent: Dec. 2, 1986

[54] ANASTOMOSIS DEVICE WITH EXCISABLE FRAME

[76] Inventor: Arnold R. Leiboff, 20 Wendell St., Hempstead, N.Y. 11550

[21] Appl. No.: 694,614

[22] Filed: Jan. 24, 1985

[51] Int. Cl.$^4$ .............................................. A61B 17/11
[52] U.S. Cl. ............................ 128/334 C; 128/334 R; 128/335.5; 604/49
[58] Field of Search ......... 604/49; 128/334 C, 334 R, 128/335, 335.5

[56] References Cited

U.S. PATENT DOCUMENTS

| | | | |
|---|---|---|---|
| 3,265,069 | 8/1966 | Healey, Jr. | 128/334 C |
| 3,316,914 | 5/1967 | Collito | 128/334 C |
| 3,561,448 | 2/1971 | Peternel | 128/334 C |
| 3,606,888 | 9/1971 | Wilkinson | 128/334 C |
| 3,771,526 | 11/1973 | Rudie | 128/334 C |
| 3,774,615 | 11/1973 | Lim et al. | 128/334 C |
| 3,974,835 | 8/1976 | Hardy, Jr. | 128/334 C |
| 4,055,186 | 10/1977 | Leveen | 128/334 C |
| 4,182,339 | 1/1980 | Hardy, Jr. | 128/334 R |
| 4,233,981 | 11/1980 | Schomacher | 128/334 C |

FOREIGN PATENT DOCUMENTS

| | | | |
|---|---|---|---|
| 0119848 | 9/1984 | European Pat. Off. | 128/334 R |
| 83/02886 | 9/1983 | PCT Int'l Appl. | 128/334 C |

Primary Examiner—Stephen C. Pellegrino
Assistant Examiner—Mark Rooney
Attorney, Agent, or Firm—Bauer & Amer

[57] ABSTRACT

The free ends of two tubular tissue members to be anastomosed are each pulled over the outside of a respective ring joined by an integral frame which holds the rings rigidly a short distance apart and sewn to the respective rings and to each other across the gap formed by the frame. When the tissue members and apparatus have been completely sewn about their circumference, the frame is cut away, and the sutures are pulled taut so that the edges of the tubular tissue members are inverted and drawn into apposition between the rings. The adjacent suture ends are then tied together with proper tension to complete the anastomosis.

16 Claims, 7 Drawing Figures

ANASTOMOSIS DEVICE WITH EXCISABLE FRAME

BACKGROUND OF THE INVENTION

The present invention relates to a method and apparatus for joining the severed ends of intestines and the like and in particular to a method and apparatus for anastomosis.

The present invention is directed to the improvement of anastomotic surgery, by enabling the surgeon to perform a more secure anastomosis, more simply and in a shorter time than heretofore. It has particular application in all types of gastrointestinal surgery including esophagogastrostomy, gastroduodenostomy and gastrojejunostomy as well as large and small bowel anastomosis, while maintaining an inverting type of anastomosis. In this type the serosa of the bowel is turned inward so that the contact of the two pieces of bowel is established on their outer, i.e. serosal, surface. The anastomosis is said to be serosa to serosa.

To assist the surgeon in making a secure, leakproof anastomosis, various devices have been developed which are inserted into the lumens of opposing tubular sections to hold them together for suturing or clamping until secured. One such type device, first developed by John B. Murphy, comprises a pair of button-like complementary clamping members, which clamp between them the spurs or end flaps of the intestine. Such devices are primarily designed to avoid the time consuming and difficult task of suturing. However, a number of difficulties and disadvantages mitigate against their use. The most disadvantageous feature of this type of device is that they depend on the maintenance of sufficient compressive force of the clamping members on the spur so that the spur is uniformly held and necrosis occurs substantially uniformly about the wall of the intestine. When uniform necrosis does not occur which is not unusual with these devices, the clamping members fail to pass out of the intestine, and since they do not dissolve or disintegrate, may cause intestinal obstruction. Another disadvantageous feature is that all these devices significantly compromise luminal clearance and, therefore, are all prone to cause some degree of intestinal obstruction while they remain in situ.

Recently, devices have been developed in which the ends of the intestines are rolled or wrapped about dissolvable and/or disintegrating ring members and held by clamping devices and/or suturing in this condition until the juncture is healed. One such device is suggested in U.S. Pat. No. 4,182,339 and another in U.S. Pat. No. 3,974,835, both in the name of Thomas G Hardy, Jr.

These devices are also not fully advantageous. The former, which relies on separate purse string sutures to keep the two bowel ends engaged together upon the anastomotic sleeve, is insecure and prone to leak, and the latter device has been found to be too awkward and difficult to apply to be of clinical use.

It is an object of the present invention to provide a device that will permit a simple, rapid anastomosis.

Another object of the present invention is to make possible simple anastomosis in parts of the body which would normally be quite time-consuming and/or difficult.

Another object of the present invention is to make possible an anastomosis which is stronger and less likely to rupture or leak.

Another object of the present invention is to make possible an anastomosis which will always maintain a widely patent lumen which cannot stenose and is therefore less likely to obstruct.

Yet a further object of the present invention is to provide a method for performing anastomotic surgery utilizing anastomotic rings that are held in fixed position by an excisable integral frame which thereby holds the tissue members to be anastomosed at a constant short distance apart while the anastomosis is being sutured allowing for good visibility and accurate stitch placement.

A further object of the present invention is to provide anastomotic rings which can be formed of a material that will disintigrate within a specified period of time.

Yet another object of the present invention is to provide anastomotic rings painted or impregnated with a radiopaque material so that postoperative radiographic evaluation of anastomotic integrity can be made by examining the relationship between the two ring images on X-ray.

Yet another object of the present invention is to provide an anastomotic apparatus that is easily handled, inexpensive, and capable of being stocked in operating rooms in quantities for immediate use.

These and other objects of the present invention will become more apparent after consideration of the following disclosure.

SUMMARY OF THE INVENTION

The invention, in preferred form, includes a pair of anastomotic rings which are coaxially joined and held a short distance apart by an integral frame. The configuration resembles two wheels fixed by two spokes each to a central axle. Each ring has a convex outer surface and a flat surface on the side facing the opposite ring.

In use, the tubular tissue members to be anastomosed are stitched around the rings of the device of the present invention, in such a fashion that when the connecting frame is cut away and the sutures pulled taught, the edges of the tissue are inverted against the flat inner surfaces of the rings and forced into tight apposition, serosa to serosa, between the ring members.

The entire apparatus is preferably molded of a material so that the rings will disintigrate in two to three weeks. In addition the rings may be painted or impreganted with a radiopaque material so that their position can be easily localized by X-ray.

The apparatus of the present invention and method of anastomosis provided herein reduces the chance of anastomotic leakage, because the ring members cause the formation of a secure circumferential water tight seal between the inverted ends of the tubular tissue members. A regular suture anastomosis leaves potential gaps between stitches, even when continuous running sutures are employed. If even minimal tissue necrosis occurs or if there is intraluminal distension with air or feces, these potential gaps may become sites of leakage of intestinal content.

The apparatus and method of anastomosis of the present invention also reduces the likelihood of anastomotic stenosis or obstruction because the rigid rings hold the intestinal lumen wide open at the anastomosis in the early healing phase, preventing shrinkage or adherence of opposite walls. Normally, when continuous sutures are employed there is a danger that if the surgeon pulls too tightly on the stuture he can severely constrict an anastomosis by a purse string effect. This invention prevents this and allows the surgeon to safely take advantage of the speedier continuous suture technique and also to apply more tension to the suture line for a more secure water tight seal without worrying about stenosis.

Full details of the present invention are set forth in the following description of the preferred embodiments and are illustrated in the accompanying drawing.

FIGURE DESCRIPTION

DESCRIPTION OF A PREFERRED EMBODIMENT

Figure 1:
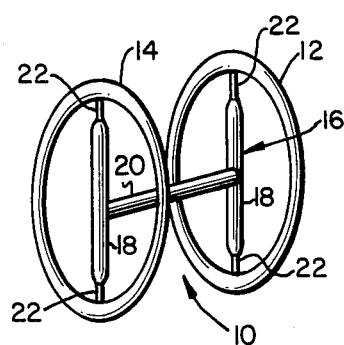
FIG. 1 is a perspective view of the anastomotic apparatus of the present invention.
Figure 6:
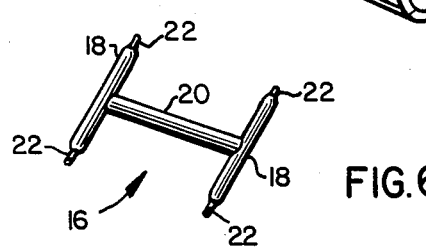
FIG. 6 is a perspective view of the excised connecting frame of the apparatus of the present invention.

The anastomotic device of the present invention is generally depicted by the numeral 10, in FIG. 1. The device comprises a pair of rings 12 and 14 which are joined together, in an integral unitary manner by an H-frame generally depicted by the numeral 16. In the illustration of the drawing, the rings are shown to be substantially identical. However, in practice, the rings need not be identical and might perform their functions better if they were not necessarily identical. The H-frame as seen in FIG. 6 comprises a pair of bars 18, extending parallel to each other and respectively forming a diametric spoke in the rings 12 and 14, respectively, and an axial cross bar 20. The ends of each of the vertical bars, i.e., spokes are reduced in diameter, forming thin struts 22 to provide an easily frangible or breakable connection with the rings. In general, the device resembles a pair of parallel disposed wheels, each having a pair of spokes and joined together by a common axle.

Figure 2:
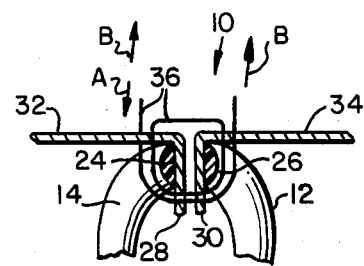
FIG. 2 is a cross-sectional view of a short segment of the ring portions of the apparatus and the sutured arrangement of the tubular tissue parts thereover.
Figure 3:
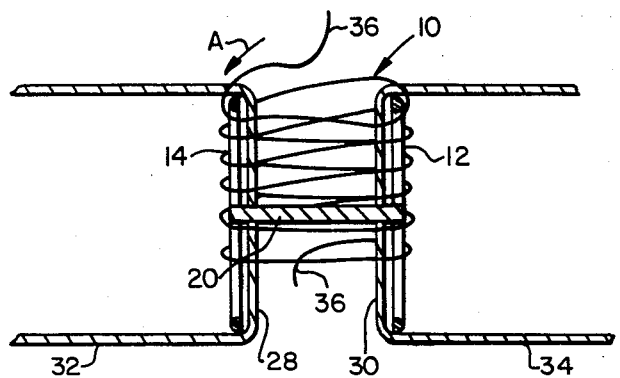
FIG. 3 is a cross-sectional view of the anastomis showing the apparatus of the present invention and the retaining stitch.
Figure 4:
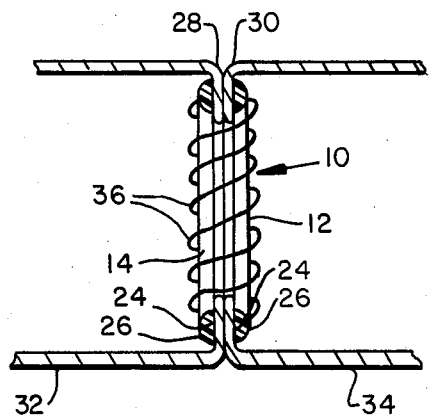
FIG. 4 is a cross-sectional view of a completed anastomosis utilizing the apparatus of the present invention.

As seen in the embodiment of FIG. 2, the rings 12 and 14 have a semicircular cross-section, comprising a flat interface 24 on the interior surface in opposition to the companion ring, and an arcuate edge 26 on the exterior surface. This cross-section provides a relatively wide area of close apposition between the two rings when the anastomosis is completed, resulting in a more secure entrapment of the spur or flap ends 28 and 30 of the tubular (i.e. intestinal or the like) sections 32 and 34 respectively which, as will be appreciated from FIGS. 3 or 4, are pulled over the outside of the corresponding rings and inverted against the respective flat edges 24.

In use, the rings 12 and 14 are secured to the respective ends of the severed tube 32 and 34 by using either multiple interrupted sutures or a continuous (or running) suture 36 or combinations thereof, which pass through the tissue wall and through the central opening in the rings. In the preferred form, the suture 36 as illustrated in FIGS. 2 and 3 involves putting a radial stitch following the single arrow A from the outside of one tubular tissue section 32, 34 behind the curved surfaces 26 of the ring 12, 14 approximately a centimeter from the cut edge, thence through the central opening of the associated ring, and back through the tissue wall in the slap or spur 28, 30 of the same tubular tissue section, inside to out near the free edge. The stitch is then carried across the gap between the rings 12 and 14 as in FIGS. 2 and 3 held spaced apart by the connecting frame 16 and sewn radially outside in through the flap or spur 28, 30 of the opposing free end of the other tubular tissue section, through the central opening of the second ring, and finally, radially out through the wall of the second tubular section behind the curved surface. A series of such stitches is made until the entire circumference is traversed. This suture technique causes the flaps or spurs 28, 30 of both open tube ends to fold over and invert between the rings 12 and 14 when the ends of the sutures are pulled.

The apparatus 10 is easier and quicker to use than prior known structures in that it is easily held in situ during the application of the stitches. In practice, an attending nurse or assistant clamps the cross bar 20 to hold the rings 12 and 14 in the sections 32 and 34 while the surgeon applies the stitches. This frees the hands of the surgeon who is now able to perform his task rapidly and accurately about the sections and their flap ends all of which are held and maintained in their open and accessible condition. Thereafter, the frame 16 may be removed to enable the closure of the rings and flaps together. At this time, the frame 16 may be cut away and removed from the rings. After the frame 16 is excised or free of the rings 12 and 14 at the struts 22, the suture is pulled taut at both its ends in the direction of double arrow B causing the tube flaps to be trapped circumferentially by and between the rings, resulting in a 360 degree water tight seal against anastomotic leakage. Whether a plurality of separate sutures about the circumference of the rings are used or a single continuous suture is used, the stitches are not pulled tight or tied until all of the sutures are placed in position circumferentially about the rings, as seen in FIG. 3, and until the H-frame 16 is removed.

Figure 5:
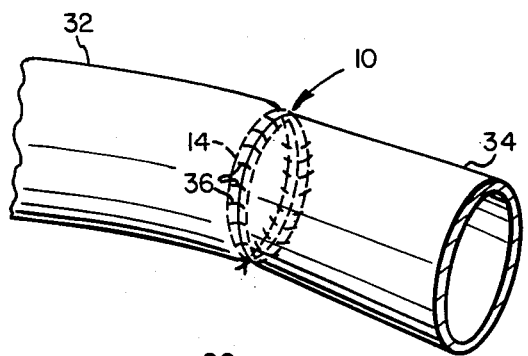
FIG. 5 is an exterior side perspective view of the completed anastomosis.

The present apparatus 10 is constructed so that the reduced junctional struts 22 where the frame 16 joins the rings 12 and 14 are thinner than the rest of the frame so that these points may be easily severed, yet the frame is sturdy and able to hold the rings rigidly in parallel planes spaced a short distance apart, during the actual process of stitching the sutures. After the sutures are made circumferentially about both tissue-ring complexes the frame 16 is excised by transecting struts 22, and is removed from within the lattice-work of the rings and sutures. Thereafter, the ends of the sutures are pulled taut, drawing together the rings 12 and 14. The adjacent suture ends are tied with some tension completing the anastomosis as seen in FIGS. 4 and 5.

Figure 7:
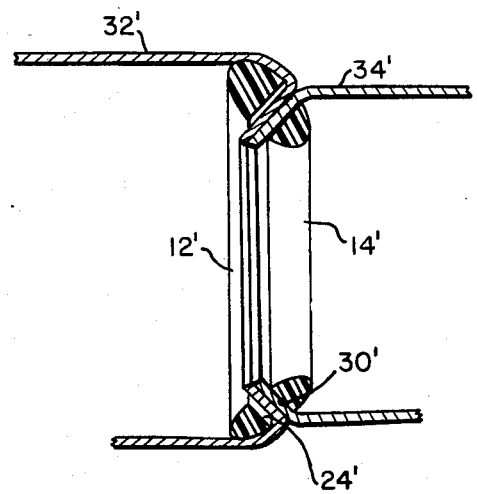
FIG. 7 is a view similar to FIG. 4, showing another embodiment of the apparatus.

In FIG. 7 an embodiment is shown which is useful when small and large tubular tissue members are to be anastomosed to each other. To insure proper fit within each lumen, one ring 12' is made larger to conform to the lumen of the larger member 32' while the other ring 14' is made smaller to conform to the lumen of smaller member 34'. The opposing interfaces 24' are set an oblique angle to the central axis of the rings 12' and 14' rather than at the substantially right angle shown in the earlier embodiment. As a result, slippage along the interfaces 24' of the rings 12' and 14' on tightening of the closing sutures about the rings of different diameter is prevented, and a secure anastomosis is obtained. The rings of this embodiment are otherwise formed as earlier described, with a connecting frame, having severable struts, and are sutured in the same way as earlier described.

It will be appreciated that aspects of both embodiments may be combined. For example, an oblique or substantially oblique direction to the central axis of the rings or interface may be provided in a set of rings of similar cross section, or a vertical interface may be provided in a set of rings which are substantially asymetrical in shape, as are the rings illustrated in FIG. 7. It is also within the scope of the invention and the teaching of obliquely directed interfaces that interfaces 24' and 30' may be positioned substantially horizontal or in a direction substantially parallel to the central axis of their respective rings.

The anastomotic apparatus 10 is preferably made by a molding process from a material which disintegrates in a specified period of time, such as polyglycolic acid, polyglactin, polydioxanone, or any other suitable bio-absorbable or bio-degradable material which will easily pass out of the body. The sutures employed in the anastomosis may also be absorbable, resulting in complete dissolution or passage of the apparatus and foreign material out of the body after the anastomosis heals. It is intended that the anastomotic apparatus be produced and available in a variety of sizes so that an anastomosis with even the smallest lumen can be constructed without need for stretching the tube unduly.

The invention is comprised basically of anastomotic rings connected by an integral frame taking the form of the embodiment described herein. However, the invention in its broader aspects is not limited to the specific embodiments herein shown and described but departures may be made therefrom, within the scope of the accompanying claims without departing from the principles of the invention and without sacrificing its chief advantages. For example, the number of "spokes" 18 per ring 12 or 14 may be increased or two or more parallel axial members may be substituted for the single "axle" 20. In addition, loops or grooves may be formed in the rings 12 or 14 to contain sutures, or the semicircular cross-section of the rings may be changed to circular, oval, or other shape.

The material from which the device is formed may be impregnated, or coated or contain as a constituent a radiopaque component so as to be visible by X-ray.

Various changes and modifications have been disclosed herein. Other narrations and embodiments as well as the changes and modifications will be readily apparent to those skilled in this art. It is, therefore, intended that the disclosure be taken as illustrative only and not limiting of the invention.

I claim:

1. An anastomosis device for surgically joining the free ends of two tubular body tissue members, said device comprising a pair of rigid rings made of bio-degradable material for placement in the lumens of the free ends of the respective tubular members, a frangible rigid frame having an essentially non-yieldable bar integrally holding said two rings in fixed substantial parallel opposition to each other at a distance spaced apart permitting the placement of the free ends of the two tubular members about the respective spaced rings, said frame being excisable from said rings upon application of sutures in a series of running stitches extending from one ring to another across the space between the opposing rings and about the free ends of the tubular members and their respective rings, said sutures permitting said rings and respective tubular members to be drawn together by pulling the ends of the stitches to retain said rings and tubular members in fixed apposition with the free ends of the tubular members clamped therebetween.

2. The device according to claim 1, wherein said rings contain radiopaque material.

3. An anastomosis device for joining the free ends of two tubular body tissue members by a running stitch, said device comprising a pair of rings for placement in the lumens of the free ends of the respective tubular members, a frame connecting and holding said two rings in opposition to each other at a distance spaced apart permitting the placement of the free ends of the two tubular members about the respective spaced rings, and the application of the running stitch about and extending between the free ends of the tubular members and their respective rings, said frame comprises at least one pair of spaced bars forming at least one radial spoke in each of said rings and a central cross bar extending axially therebetween, said radial bars have ends attached to the respective rings and being excisable from said rings permitting said rings and respective tubular members to be drawn together by pulling the ends of the running stich to retain said rings and tubular members in fixed apposition with the free ends of the tubular members clamped therebetween.

4. The device according to claim 3 wherein said ends of said radial bars are reduced and attached to the respective ring facilitating excision of said frame.

5. The device according to claim 1 wherein said rings have a convex outer surface and a flat inner surface on the side facing the opposing ring.

6. The device according to claim 5 wherein the inner surfaces are at substantially oblique angles to the central axes of the rings.

7. The device according to claim 5 wherein the inner surfaces are at substantially right angles to the central axes of the rings.

8. The device according to claim 5 wherein the inner surfaces are substantially parallel to the central axes of the rings.

9. The method for joining the two free ends of a severed tubular tissue member, comprising the steps of inserting into the lumen of one of the free ends the first of a pair of rings and into the other of said free ends the second of the pair of rings, so that the lumen of each free end is inverted over the respective rings to form lumen spurs, holding the pair of rings and lumen spurs spaced apart by a connecting frame and applying at least one running suture in a plurality of spaced open stitches to extend from one ring to the other and about the circumferences of both the rings, passing serially through both the walls and lumen spurs of the free ends of the tubular members and their respective rings, removing the connecting frame, and pulling the stitches to draw said rings together to hold and secure together said inverted lumen spur free ends between said rings.

10. The method according to claim 9 wherein said stitches are formed by insertion of a suture initially radially through the wall of one of the tubular members into the lumen thereof, through the central opening in the associate ring and outward through the lumen spur, and thence through the lumen spur of the other tissue member, the central opening of the associated ring and outward of the wall of said other members.

11. The method according to claim 10 wherein said stitches are formed of a single suture looped in a continuous series of stitches, about the circumference thereof.

12. The method according to claim 11 wherein said rings are drawn together by pulling on the front and rear ends of said suture.

13. The method according to claim 9 wherein said rings have relatively flat interfaces lying in opposition to each other, and the method includes the step of placing the tubular member serosa to serosa over said flat interfaces.

14. The method according to claim 13 wherein said interfaces are at substantially oblique angles to the central axes of the rings.

15. The method according to claim 13 wherein said interfaces are substantially at rignt angles to the central axes of the rings.

16. The method according to claim 13 wherein said interfaces are substantially parallel to the central axes of the rings.

* * * * *